(12) United States Patent
Gunaratne (10) Patent No.: US 10,583,842 B1
(45) Date of Patent: Mar. 10, 2020

(54) DRIVER STATE DETECTION BASED ON GLYCEMIC CONDITION

(71) Applicant: Toyota Motor Engineering & Manufacturing North America, Inc., Plano, TX (US)

(72) Inventor: Pujitha Gunaratne, Northville, MI (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 0 days.

(21) Appl. No.: 16/150,506

(22) Filed: Oct. 3, 2018

Related U.S. Application Data (60) Provisional application No. 62/725,762, filed on Aug. 31, 2018.

(51) Int. Cl.
   *B60W 40/09* (2012.01)
   *A61B 5/145* (2006.01)
   (Continued)

(52) U.S. Cl.
   CPC ......... *B60W 40/09* (2013.01); *A61B 5/14532* (2013.01); *B60W 50/12* (2013.01);
   (Continued)

(58) Field of Classification Search
   USPC ...................................................... 340/439
   See application file for complete search history.

(56) References Cited

U.S. PATENT DOCUMENTS

| | | | |
|---|---|---|---|
| 5,942,979 A | 8/1999 | Luppino | |
| 7,266,430 B2 * | 9/2007 | Basson | B60K 28/066 340/438 |

(Continued)

FOREIGN PATENT DOCUMENTS

| | | |
|---|---|---|
| CN | 105662430 A | 6/2016 |
| CN | 105539320 B | 11/2016 |

(Continued)

OTHER PUBLICATIONS

"Driving with diabetes in the future: in-vehicle medical monitoring"; https://www.ncbi.nlm.nih.gov/pmc/articles/PMC2864183/, Accessed/Published Date: Mar. 1, 2010.

(Continued)

*Primary Examiner* — Emily C Terrell
(74) *Attorney, Agent, or Firm* — Dinsmore & Shohl LLP (57) ABSTRACT

Embodiments of the disclosure relate to systems and methods for detecting driver state based on glucose levels of a driver of the vehicle. In one embodiment, a method of detecting driver state based on glucose levels of a driver of the vehicle includes receiving measurements of glucose levels of the driver from a continuous glucose monitoring (CGM) device and determining a glycemic state of the driver based on the measurements and a driving performance parameter based on the glycemic state. The method further includes determining a degree of impairment of the driver based on whether the driving performance parameter satisfies a predetermined threshold and determining a level of driver state severity based on driver performance characteristics, features of the driving environment, and the degree of impairment of the driver. A response is then activated based on the driver state severity.

20 Claims, 4 Drawing Sheets

(51) Int. Cl.
*B60W 50/12* (2012.01)
*G05D 1/00* (2006.01)
*G06N 20/00* (2019.01)
*B60W 40/08* (2012.01)

(52) U.S. Cl.
CPC ......... *G05D 1/0061* (2013.01); *G05D 1/0088* (2013.01); *G06N 20/00* (2019.01); *B60W 2040/0818* (2013.01); *B60W 2040/0872* (2013.01)

(56) References Cited

U.S. PATENT DOCUMENTS

| | | | |
|---|---|---|---|
| 8,207,859 B2 | 6/2012 | Enegren et al. | |
| 2007/0112261 A1 | 5/2007 | Enegren et al. | |
| 2008/0015422 A1 | 1/2008 | Wessel | |
| 2009/0156915 A1 | 6/2009 | Cross | |
| 2009/0270705 A1* | 10/2009 | Enegren | A61B 5/0031 600/365 |
| 2013/0070043 A1* | 3/2013 | Geva | B60K 28/066 348/14.02 |
| 2014/0240132 A1* | 8/2014 | Bychkov | A61B 5/18 340/576 |
| 2014/0276090 A1* | 9/2014 | Breed | A61B 5/18 600/473 |
| 2017/0308666 A1 | 10/2017 | Thomson et al. | |
| 2017/0372011 A1 | 12/2017 | Noeth | |

FOREIGN PATENT DOCUMENTS

| | | | |
|---|---|---|---|
| JP | 2006301963 A | 11/2006 | |
| WO | WO-2018145965 A1 * | 8/2018 | ............... A61B 5/01 |

OTHER PUBLICATIONS

"3 ways ford cars could monitor your health"; https://spectrum.ieee.org/the-human-os/biomedical/diagnostics/3-ways-ford-cars-could-monitor-your-health, Accessed/Published Date: May 19, 2017.

Merickel, et al., "Driving Safety and Real-Time Glucose Monitoring in Insulin-Dependent Diabetes", Society of Automotive Engineers of Japan, Inc., 2017.

* cited by examiner

DRIVER STATE DETECTION BASED ON GLYCEMIC CONDITION

TECHNICAL FIELD

The present specification generally relates to the field of health monitoring of a vehicle driver and, more specifically, to systems and methods for detecting glycemic condition of a vehicle driver and then using the information to determine whether/when/how to intervene.

BACKGROUND

Diabetes affects greater than 8.5% of adults globally, representing 422 million adults worldwide. This number is projected to increase to 642 million diagnosed adults worldwide by 2040 and, considering estimates that 45.8% of diabetes cases are undiagnosed, the number affected by 2040 may be over one billion. Onset of diabetes mellitus (DM) may affect a person's ability to drive a vehicle. In particular, hypoglycemia (low glucose level) is a key factor affecting the ability to drive, particularly in insulin-dependent DM because it leads to higher levels of blood pressure, sleep apnea, etc. While insulin is essential for survival in many patients with DM, close control over hyperglycemia (high glucose level), which reduces long-term complications of diabetes (retinopathy, neuropathy, renal disease, and cerebrovascular disease), can increase the risk of hypoglycemia.

Hypoglycemia and patterns of poor glucose control can impair the cognitive abilities (attention, memory, and decision-making) needed for performing complex tasks such as vehicle driving. When the glucose level falls below a certain threshold, these impairments can reduce driver performance. Cognitive impairments from hypoglycemia (particularly attention and executive dysfunction) can persist for hours after glucose levels return to normal. In drivers with DM, these impairments include self-awareness of internal physiological state. Self-awareness of internal physiological state (an executive function) may affect a driver's ability to mitigate risk. In normal functioning, the body releases epinephrine in response to hypoglycemia, producing autonomic effects that include increased heart rate. These autonomic effects provide internal cues to a driver with DM that he or she is impaired. Drivers affected with DM may be unable to recognize their hypoglycemic status and mitigate risk appropriately.

SUMMARY

The present specification relates to systems and methods for detecting driver state based on glucose levels of a driver of the vehicle. In one embodiment, a method of detecting driver state based on glucose levels of a driver of the vehicle is disclosed. The method includes receiving measurements of glucose levels of the driver from a continuous glucose monitoring (CGM) device and determining a glycemic state of the driver based on the measurements and a driving performance parameter based on the glycemic state. The method further includes determining a degree of impairment of the driver based on whether the driving performance parameter satisfies a predetermined threshold and determining a level of driver state severity based on driver performance characteristics, features of the driving environment, and the degree of impairment of the driver. A response is then activated based on the driver state severity.

In another embodiment, a system of driver state detection based on glucose levels of a driver of the vehicle is disclosed. The system includes a CGM device configured to sense and make measurements of glucose levels of the driver. The CGM device includes a transmitter configured to transmit the measurements of glucose levels of the driver. The system further includes a driver monitoring system communicatively coupled to the CGM device. The driver monitoring system includes one or more computing devices communicatively coupled to a receiver. Each of the one or more computing devices include a processor and a non-transitory computer-readable memory storing a machine-readable instruction set that when executed by the processor causes the driver monitoring system to perform at least a number of steps. The steps consist of receiving measurements of glucose levels of the driver from the transmitter; determining a glycemic state of the driver based on the measurements and a driving performance parameter based on the glycemic state; determining a degree of impairment of the driver based on whether the driving performance parameter satisfies a predetermined threshold; determining a level of driver state severity based on driver performance characteristics, features of the driving environment, and the degree of impairment of the driver; and activating a response based on the driver state severity.

In yet another embodiment, a driver monitoring system is disclosed. The driver monitoring system includes one or more computing devices communicatively coupled to a CGM device. Each of the one or more computing devices include a processor and a non-transitory computer-readable memory storing a machine-readable instruction set that when executed by the processor causes the driver monitoring system to perform at least a number of steps. The steps consist of receiving measurements of glucose levels of a driver from the CGM device; determining a glycemic state of the driver based on the measurements and a driving performance parameter based on the glycemic state; determining a degree of impairment of the driver based on whether the driving performance parameter satisfies a predetermined threshold; determining a level of driver state severity based on driver performance characteristics, features of the driving environment, and the degree of impairment of the driver; and activating a response based on the driver state severity. The driver monitoring system further includes a messaging system configured to generate a message to alert a recipient if the driver state severity exceeds a predetermined level.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

While it is known that DM affects a person's ability to drive, the degree of glucose control needed to produce stable real-world driving performance in drivers with DM is unknown. To mitigate accident risk due to DM, the degree of effective glucose control for individuals may be determined such that the driving ability can be improved in a timely manner while driving. While a single hypoglycemic episode affects surrogate measures of driver risk such as cognitive performance, vigilance scores, and simulated driving performance, the effects on real-world driving behavior are poorly understood. Better understanding of how these factors influence real-world driving may be beneficial for mitigating accident risk in drivers with DM. Technological advances can be used to enable the direct assessment of real-world driving behavior with in-the-field physiological measurements and continuous glucose monitoring (CGM). Embodiments described herein are directed to systems and methods for detecting glucose levels and physiological parameters such as body temperature, drowsiness, blood pressure, heart rate, respiratory rate, blood oxygen level, electroencephalographic activity, electromyography activity, gastric activity, etc. of a vehicle driver. The measurements of glucose levels and the physiological parameters are then fed into a driver monitoring system, which determines whether/when/how to intervene.

The glucose level of the driver is measured using a continuous glucose monitoring (CGM) device. The driver monitoring system determines the glycemic state of the driver based on the measurements and a degree of driver responsiveness based on the glycemic state. The driver monitoring system then determines a degree of impairment of the driver based on the degree of the driver responsiveness. The driver monitoring system predicts a level of severity of the driver state, based on the degree of impairment, features of the driving environment and driver performance characteristics based on patterns between driving performance and glucose levels and other physiological parameters over time. If the driver monitoring system determines that the driver state is highly or moderately severe, it activates a response which may include generating a warning or an emergency alert and even transferring control of the vehicle from a driver mode to an autonomous mode, in the event the driver state is determined to be highly severe.

Figure 1:
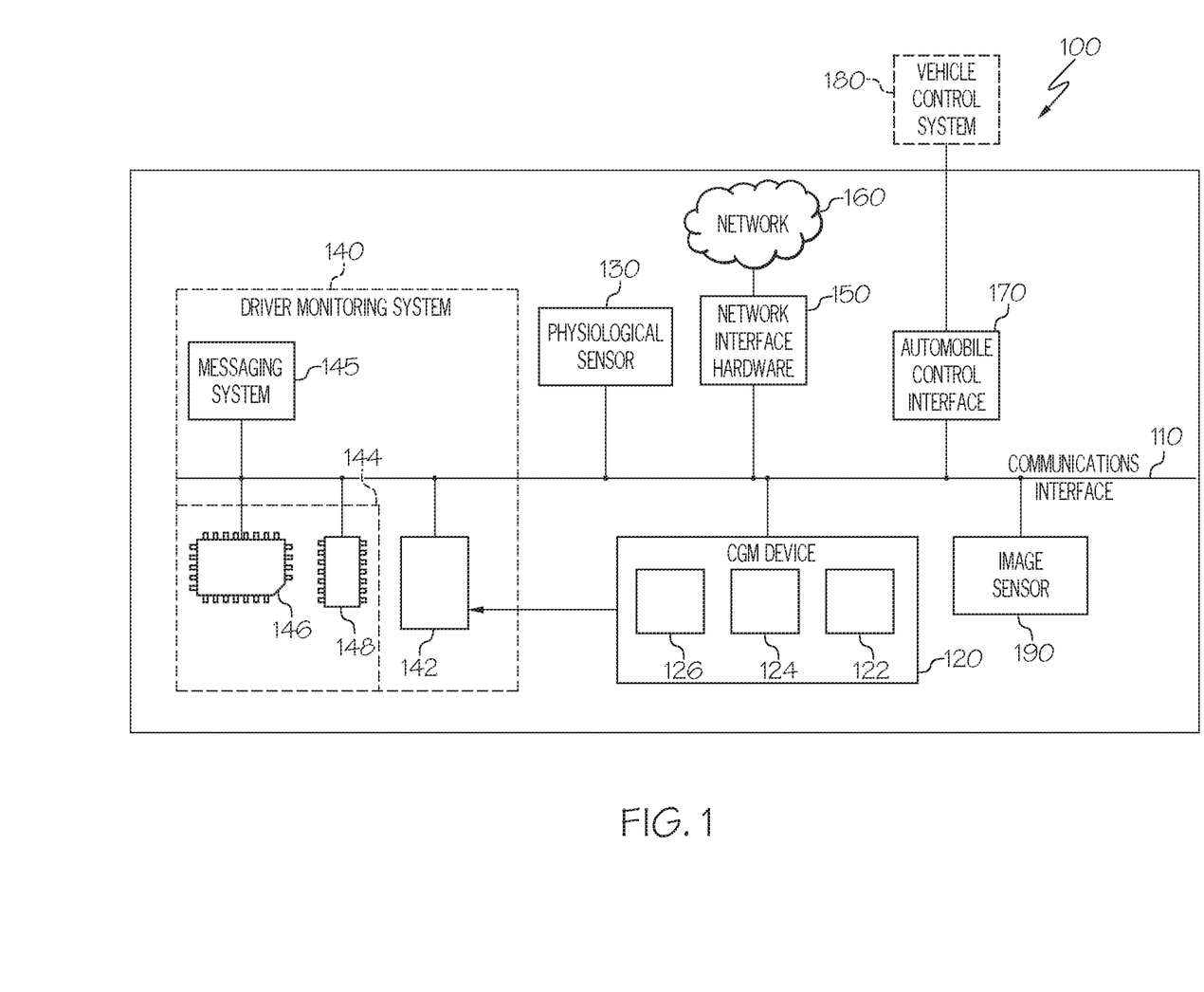
FIG. 1 depicts a system of driver state detection based on glucose levels of a driver of the vehicle, according to one or more embodiments shown and described herein.

FIG. 1 depicts a system 100 of driver state detection based on glucose levels of a driver of the vehicle. The system 100 generally includes a communication path 110, a CGM device 120, one or more physiological sensors 130, a driver monitoring system 140, a network interface hardware 150, a vehicle control interface 170 and an image sensor 190. The system 100 may be communicatively coupled to a network 160 by way of the network interface hardware 150. The components of the system 100 may be physically coupled or may be communicatively and operably coupled through the communication path 110 and/or the network 160.

The communication path 110 is formed from any medium that is capable of transmitting a signal such as, for example, conductive wires, conductive traces, optical waveguides, or the like. The communication path 110 may also refer to the expanse in which electromagnetic radiation and their corresponding electromagnetic waves traverses. Moreover, the communication path 110 may be formed from a combination of mediums capable of transmitting signals. In one embodiment, the communication path 110 comprises a combination of conductive traces, conductive wires, connectors, and buses that cooperate to permit the transmission of electrical data signals to and from the various components of the system 100 such as the CGM device 120, the one or more physiological sensors 130, the driver monitoring system 140, the network interface hardware 150, the vehicle control interface 170, the image sensor 190 and the like. Accordingly, the communication path 110 may comprise a bus. Additionally, it is noted that the term "signal" means a waveform (e.g., electrical, optical, magnetic, mechanical or electromagnetic) capable of traveling through a medium such as DC, AC, sinusoidal-wave, triangular-wave, square-wave, vibration, and the like.

Figure 2A:
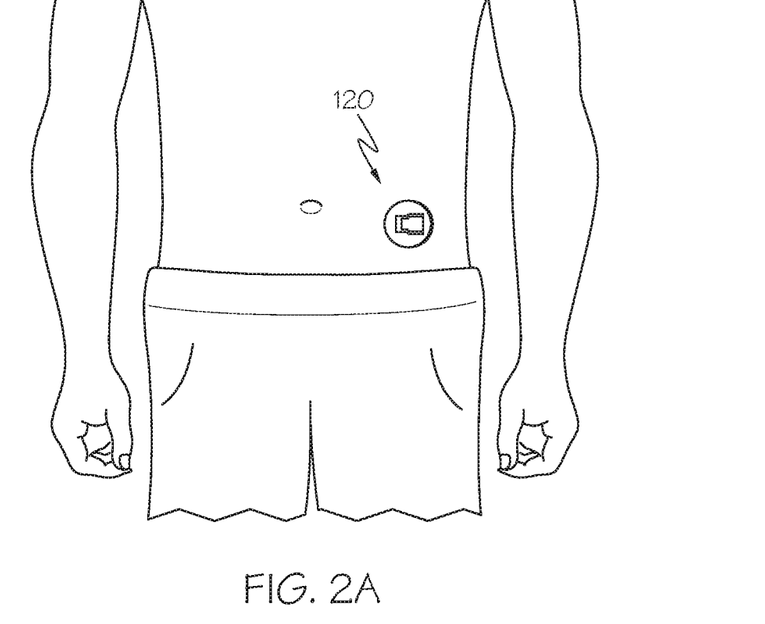
FIG. 2A depicts a perspective view of a CGM device placed on a human body, according to one or more embodiments shown and described herein.
Figure 2B:
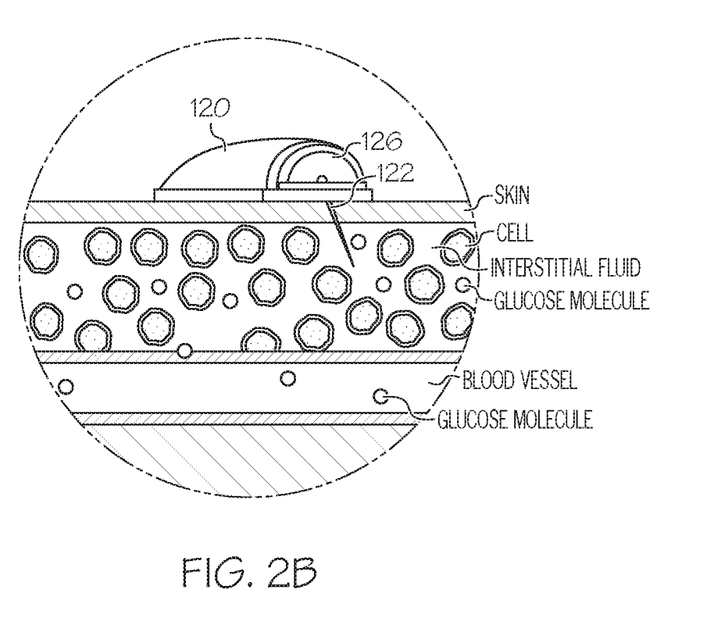
FIG. 2B depicts a cross-sectional view of a CGM device placed the human body, according to one or more embodiments shown and described herein.

The CGM device 120 includes a CGM sensor 122, a CGM measuring component 124 and a transmitter 126. FIGS. 2A and 2B depict a perspective view and a cross-sectional view of an example CGM device 120 placed on a human body. The CGM device 120 is worn on a human body with the CGM sensor 122 inserted into the skin of the human body. In the embodiment shown in FIG. 2A, the CGM device 120 is worn on the abdomen. As shown in FIG. 2B, the CGM sensor 122 of the example CGM device 120 is a very thin metallic filament that is inserted just below the skin to detect glucose levels in the subcutaneous interstitial fluid filling the gap between the skin and the blood vessel. It should be understood that other configurations of the CGM device 120 are also possible. The CGM sensor 122 provides detailed real-time data streams of glucose levels in the interstitial fluid under the skin. While in some embodiments, the glucose levels may be sampled every 5 minutes from the interstitial fluid, the CGM device 120 may not be limited as such. The glucose level sensed by the CGM sensor 122 is measured by the CGM measuring component 124. The transmitter 126 is configured to transmit the measurements of glucose levels of the driver to a receiver 142 within the driver monitoring system 140, which accumulates a historical data on glucose levels of the driver. The transmission may occur over the communication path 110 or via Bluetooth or radio frequency communication. It should be noted that the CGM device 120 is not limited to that shown in FIGS. 2A and 2B and described herein. Any other known or yet-to-be-developed CGM device may be used.

Referring to FIG. 1 again, the one or more physiological sensors 130 are communicatively coupled to the driver monitoring system 140 through the communication path 110 and/or the network 160. The one or more physiological sensors 130 may be a wearable sensor worn by the driver of the vehicle or a singular or plurality of sensors coupled to the seat, the steering wheel or other parts of the vehicle. The one or more physiological sensors 130 are configured to measure physiological parameters of the driver continuously during the operation of the CGM device 120. The physiological parameters may include, but are not limited to, body temperature, drowsiness, blood pressure, heart rate, respiratory rate, blood oxygen level, electroencephalographic activity, electromyography activity, gastric activity, etc. In some embodiments, the one or more physiological sensors 130 may be a commercial wearable wristwatch-like sensor such as those manufactured by FitBit™ and Garmin™. The measurements of physiological parameters of the driver are transmitted by the one or more physiological sensors 130 to the receiver 142 in the driver monitoring system 140.

The driver monitoring system 140 includes the receiver 142, a messaging system 145 coupled to the communication path 110 and/or the network 160 and a computing device 144 comprising a processor 146 and a non-transitory computer-readable memory 148. The receiver 142 is configured to receive measurements of glucose levels of the driver from the transmitter 126 in the CGM device 120 and measurements of physiological parameters of the driver from the one or more physiological sensors 130. The messaging system 145 is configured to display real-time measurements of the glucose level, the physiological parameters, a degree of impairment and a level of driver state severity as well as to generate a message to alert a recipient if the driver state severity exceeds a predetermined level, as described in more detail herein.

The processor 146 may be any device capable of executing a machine-readable instruction set stored in the non-transitory computer-readable memory 148. The machine-readable instruction set is represented by the flowchart 300 (embodiment shown in FIG. 3). Accordingly, the processor 146 may be an electronic controller, an integrated circuit, a microchip, a computer, and the like. The processor 146 is communicatively coupled to the other components of the system 100 by the communication path 110. Accordingly, the communication path 110 allows the components coupled to the communication path 110 to operate in a distributed computing environment. Specifically, each of the components of the system 100 may operate as a node that may send and/or receive data.

The non-transitory computer-readable memory 148 of the system 100 is coupled to the communication path 110 and communicatively coupled to the processor 146. The non-transitory computer-readable memory 148 may comprise RAM, ROM, flash memories, hard drives, or any non-transitory memory device capable of storing the machine-readable instruction set such that the machine-readable instruction set can be accessed and executed by the processor 146. The machine-readable instruction set may comprise logic or algorithm(s) written in any programming language of any generation (e.g., 1GL, 2GL, 3GL, 4GL, or 5GL) such as, for example, machine language that may be directly executed by the processor 146, or assembly language, object-oriented programming (OOP), scripting languages, microcode, etc., that may be compiled or assembled into machine readable instructions and stored in the non-transitory computer-readable memory 148. Alternatively, the machine-readable instruction set may be written in a hardware description language (HDL), such as logic implemented via either a field-programmable gate array (FPGA) configuration or an application-specific integrated circuit (ASIC), or their equivalents. Accordingly, the functionality described herein may be implemented in any conventional computer programming language, as pre-programmed hardware elements, or as a combination of hardware and software components. While the embodiment depicted in FIG. 1 includes a single non-transitory computer-readable memory 148, other embodiments may include more than one.

The image sensor 190 is configured to capture images of the driver's face, upper body and feet. The image sensor 190 is also configured to capture images of the surrounding driving environment including surrounding cars, traffic signs and signals, lane markers and any obstacles on the road. In some embodiments, the image sensor 190 may be an infrared camera, though it is not limited as such. The image sensor 190 provides the images of the driver's face, upper body and feet as well as the images of the surrounding driving environment to the driver monitoring system 140.

Referring back to FIG. 1, the network interface hardware 150 may include and/or be configured for communicating with any wired or wireless networking hardware, including an antenna, a modem, a LAN port, wireless fidelity (Wi-Fi) card, WiMax card, ZigBee card, Bluetooth chip, USB card, mobile communications hardware, and/or other hardware for communicating with other networks and/or devices.

The network 160 may be a wide area network (wired or wireless), such as a cloud network, the internet, a cellular network, or other communications network for communicating devices across a wide area. Additionally or alternatively, the network 160 may be a wired or wireless local area network for communicating the data, such as via a local area network, near field communication (NFC), Bluetooth, wireless fidelity (Wi-Fi).

The vehicle control interface 170 provides an interface between the components of the system 100 to a vehicle control system 180. The vehicle control interface 170 is configured to transfer control between a driver mode and an autonomous mode based on a determination by the driver monitoring system 140 regarding the glycemic state and the driving ability of driver of the vehicle.

Figure 3:
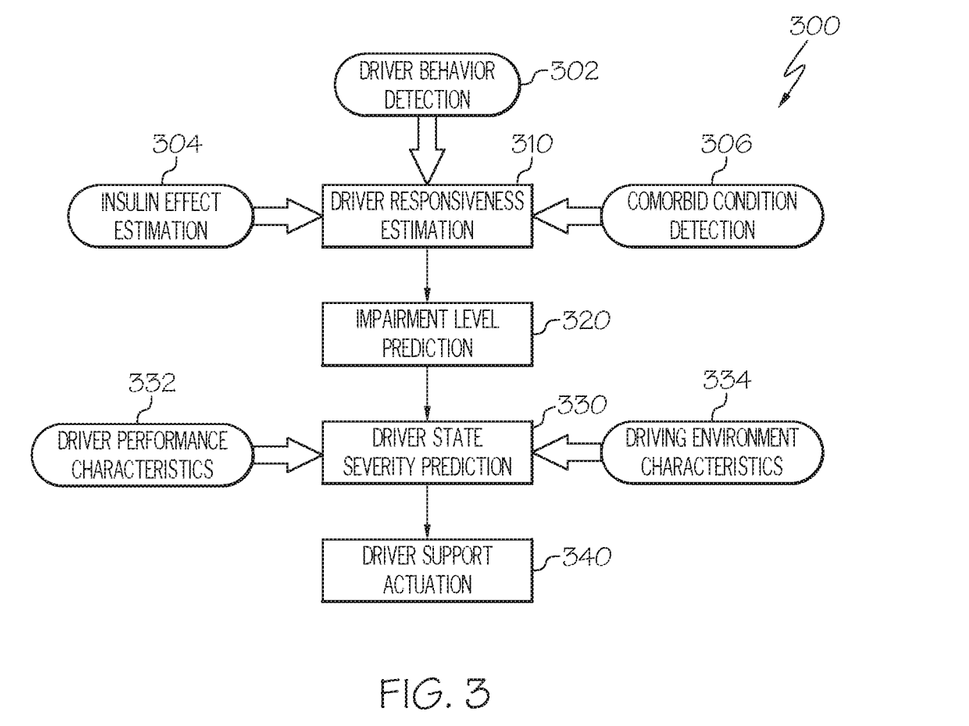
FIG. 3 depicts a flowchart representing an embodiment of a machine-readable instruction set used by the system for controlling the vehicle based on glucose levels of a driver of the vehicle, according to one or more embodiments shown and described herein.

FIG. 3 depicts a flowchart 300 representing an embodiment of the machine-readable instruction set used by the system 100 for detecting driver state based on glucose levels of a driver of the vehicle. The machine-readable instruction set includes a driver responsiveness estimation module 310, an impairment level prediction module 320, a driver state severity prediction module 330 and a driver support actuation module 340. The driver responsiveness estimation module 310 accepts input from the insulin effect estimation module 304. Optionally, the driver responsiveness estimation module 310 may also accept additional inputs from the driver behavior detection module 302 and the comorbid condition detection module 306. The driver state severity prediction module 330 accepts inputs from the driver performance characteristics module 332 and the driving environment characteristics module 334.

The driver behavior detection module 302 receives images of the driver's face, upper body, and feet captured using the image sensor 190. The driver behavior detection module 302 then applies computer vision tools to extract facial and whole-body features indicating the driver behavior and posture at any given time. The driver behavior detection module 302 estimates and classifies the different patterns of driver behavior and posture using one or more machine learning algorithms. In some embodiments, the driver behavior detection module 302 uses a computer vision tool such as OpenPose to extract features of the face, upper body, legs and feet and estimate in real-time the driver behavior and posture. For example, the driver behavior detection module 302 may determine that the driver is drowsy, inattentive, restless or otherwise not in an appropriate driving posture, based on the features extracted by OpenPose. Non-limiting examples of detection of driver behavior and posture may be found in U.S. patent application Ser. No. 15/861,009 filed Jan. 3, 2018, assigned to Toyota Research Institute, Inc. and titled "Vehicle Systems and Methods for Detecting and Mitigating an Incapacitated Driver", the entire contents of which are incorporated herein by reference. The driver behavior and posture thus estimated is then inputted to the driver responsiveness estimation module 310.

The insulin effect estimation module 304 receives measurements of glucose levels and physiological parameters of the driver from the receiver 142. The insulin effect estimation module 304 may then optionally evaluate the measurements against any dose of insulin pumped to the body of the driver by an insulin pump. Otherwise, the measurements of glucose levels and physiological parameters of the driver are inputted to the driver responsiveness estimation module 310. The measurements of physiological parameters may include body temperature, drowsiness, blood pressure, heart rate, respiratory rate, blood oxygen level, electroencephalographic activity, electromyography activity, gastric activity, etc.

The comorbid condition detection module 306 detects comorbid conditions like obesity, sleep deprivation, lack of activity, etc. of the driver. In some embodiments, the comorbid condition detection module 306 receives weight measurements from a weighing device embedded in the vehicle such as, but not limited to a pressure sensor embedded in the seat of the vehicle. In other embodiments, the comorbid condition detection module 306 receives weight measurements from a commercially available weighing machine that are uploaded to the network 160. The weight measurements are then inputted to the driver responsiveness estimation module 310

The driver performance characteristics module 332 includes data related to driver performance characteristics such as driver steering handling, breaking and acceleration timing in different traffic conditions. This data is accumulated from a number of sources and compiled. In some embodiments, real-world driving behavior in drivers with DM is quantified by gathering data related to driving performance and using machine learning to find predictive patterns within the data such as relationships between driver error and glucose levels and other physiological parameters over time. For example, a sample of drivers with DM and drivers without DM were monitored continuously over a certain period through CGM sensors, heart rate sensors and other activity-monitoring sensors. The monitored data was collected and post-processed to inspect for proper sensor function, eliminate spurious values and physiologically impossible glucose levels. In addition, driving performance data was gathered for both sets of drivers from real-time data obtained using commonly known vehicle sensors that measure location, speed, and acceleration as well as from records at the Department of Motor Vehicles (DMV), including history of crash and citation records. The monitored data and the driving performance data formed the experimental dataset that was then fed into a machine learning algorithm in the driver performance characteristics module 332. The machine learning algorithm is designed to analyze and find predictive patterns between driving performance and glucose levels/other physiological parameters over time.

The driver performance characteristics module 332 is thus capable of determining any deviation from normal expected driver behavior, whether the driver is able to recognize the deviation and whether that deviation is caused by changes in glucose levels or other physiological factors, sleep deprivation or due to inherent risky tendencies of the driver (based on the DMV record). The predictive patterns between driving performance (including driving errors) and glucose levels and other physiological parameters over time are used to determine driver performance characteristics, which are then inputted to the driver state severity prediction module 330.

The driving environment characteristics module 334 detects features of the driving environment based on images of the surrounding driving environment captured by the image sensor 190. In some embodiments, image processing techniques based on deep-learning are used to identify ego vehicle proximity to surrounding cars, recognize traffic signs and signals, detect lane markers and vehicle position relative to the lane markers, and surrounding traffic. In some embodiments, commonly known Geographical Information Systems (GIS) databases are used to incorporate data on road speed limit, road lane numbers and width, road class (type, surface, zone) and average traffic density. The driving environment characteristics module 334 automatically extracts critical roadway features in the driving environment and contextualizes driver behavior relative to these features. The driving environment characteristics module 334 also determines and classifies lighting and weather conditions from video data collected during real-world driving to further contextualize the driving environment.

In some embodiments, the driving environment characteristics module 334 uses feature-extraction techniques such as deep-learning convolutional neural network model (DCNN) to process video data and detect roadway features. The DCNN-based vision algorithm decouples object recognition into two main tasks—localization and classification. Localization may be performed by generating class-independent proposed regions with a Selective Search algorithm (Object Detection—Prediction Object Localization) and extracting feature descriptors on the proposed regions, using a trained DCNN model, after warping the proposed regions to a fixed size. The Selective Search algorithm combines segmentation and exhaustive search, two traditionally known approaches for object localization in images. Selective search algorithms exploit the hierarchical structure of the image (segmentation) with the aim of generating all possible object locations (exhaustive search). The Selective Search algorithm uses hierarchical grouping to deal with all possible object scales. Then, the color space of the image is used to account for different invariance properties. Finally, Selective Search algorithm uses region-based similarity functions to address object variance quickly and accurately. Each proposed region generated by the Selective Search algorithm may be then classified through a linear support vector machine (SVM). For each frame of the video data processed, an output is returned indicating which of the object classes was detected. The Selective Search and SVM techniques described above can be replaced by any comparable localization and classification machine learning algorithms for DCNN to obtain object classes in the video. The features of the driving environment captured by the driving environment characteristics module 334 are then inputted to the driver state severity prediction module 330.

The driver responsiveness estimation module 310 receives estimated driver behavior and posture from the driver behavior detection module 302, the measurements of glucose levels and physiological parameters of the driver from the insulin effect estimation module 304 and weight measurements of the driver from the comorbid condition detection module 306. The driver responsiveness estimation module 310 classifies the information received from the inputs into different driver states and corresponding characteristics based on the inputs. Additionally, the driver responsiveness estimation module 310 may identify and extract functional and other relevant features of the driver from the inputs, including physiological factors such as age, to further quantify the driver states that may affect driver risk behavior in drivers with DM.

The different driver states due to various glucose levels in the driver are the different glycemic states of the driver, which may be severely hypoglycemic (less than 56 mg/dL), hypoglycemic (56-70 mg/dL), euglycemic (71-179 mg/dL), hyperglycemic (180-300 mg/dL) and severely hyperglycemic (greater than 300 mg/dL) based on different ranges of glucose levels measured.

The driver responsiveness estimation module 310 may also measure and interpret glucose variability (GV), which strongly correlates with risks of hypoglycemia and hyperglycemia. Measurement of GV requires measurement of amplitude, timing and slope of glucose levels measured with the CGM device 120. Robust order statistical (ROS) method is used for calculating GV in the presence censored blood glucose levels. The ROS method imputes censored data, which can otherwise result in biased estimate of GV, on the original scale to permit accurate characterization of driver glycemic state given CGM censoring. The ROS method imputes censored observations on the log scale and back transforms to the original scale by exponentiating the imputed values. Using the data with the observed and imputed values, GV can be calculated using standard deviation (SD), mean amplitude of glucose excursion (MAGE), mean absolute glucose change (MAGC), or any other desired statistical technique. While the ROS method estimator uses a distributional assumption only to impute the censored values, the uncensored values are used as observed.

The driver responsiveness estimation module 310 utilizes the three inputs to estimate in real-time a degree of responsiveness of the driver, which is a driving performance parameter. In some embodiments, the driver responsiveness estimation module 310 may take samples of the inputs over a given time to estimate the degree of responsiveness of the driver. The degree of responsiveness of the driver may be related to vehicle acceleration variability, vehicle braking variability, and variability in detecting and negotiating road conditions.

The impairment level prediction module 320 is configured to compare the estimated degree of responsiveness of the driver with a database of human responsiveness in different physical and physiological parameters to determine a degree of impairment of the driver at any given time. The impairment level prediction module 320 gives particular attention to severely low glucose condition, severely high glucose condition and a condition where the glucose variability of the driver fluctuates considerably over time as these conditions are known to significantly affect the responsiveness of the driver. The degree of impairment is based on whether the degree of responsiveness of the driver satisfies a predetermined threshold. The predetermined threshold relates to a range of driver responsiveness such that different levels of impairments are determined based on whether the driver responsiveness is above, within or below the range. As an example, if the impairment level prediction module 320 observes that under a specific set of physical and physiological conditions, the driver responsiveness is greater than 95%, it may determine that the driver is not impaired; similarly, if the driver responsiveness is less than 95% but greater than 75%, it may determine that the driver is mildly impaired and if the driver responsiveness is less than 75%, it may determine that the driver is impaired.

The driver state severity prediction module 330 is configured to analyze the degree of impairment of the driver at any given time with the driver performance characteristics as well as the features of the driving environment to predict, in real-time, the severity of the driver state and an associated risk-level with the driver state affecting driving performance. As an example, if the driver is determined by the impairment level prediction module 320 as being impaired, the driver state severity prediction module 330 may determine that the driver state is highly severe and the drive is incapable of controlling the vehicle under any traffic conditions. If the driver is determined by the impairment level prediction module 320 as being mildly impaired, the driver state severity prediction module 330 may determine that the driver state is moderately severe and the driver is capable of driving in light traffic conditions but not capable of driving under medium and heavy traffic conditions. If the driver is determined by the impairment level prediction module 320 as not impaired, the driver state severity prediction module 330 may determine that the driver state is not severe and the driver is capable of driving under any traffic conditions.

In some embodiments, the driver state severity prediction module 330 may implement machine learning and/or statistical techniques to support automated processing of big data on driver performance characteristics inputted from the driver performance characteristics module 332 and features of the driving environment inputted from the driving environment characteristics module 334. For example, the big data on driver performance characteristics and features of the driving environment is predictively modeled using techniques such as analysis of traffic conflicts, big data analytics, support vector machine (SVM) with recursive feature elimination (RFE), statistical modeling methods for hypothesis testing and time-series data and the like. This enables the identification of correlation and causation between the driver's state (physiology, demographics and health, cognitive function, and activity patterns) and the probability of changes in driver risky behavior in real-time, given the dynamics of the driving environment. This contextualized data is then used to predict the risk level associated with the driver state from anomalous patterns, in real-time, in multi-modal (comprising physiological, video, cognitive, in-vehicle sensors, and physiological activity data) driver behavior and driver state data across a range of driving environment dynamics.

The driver support actuation module 340 is configured to activate a response based on the severity of the driver state, including a null response if the driver state severity prediction module 330 determines that the driver is capable of driving. The driver support actuation module 340 may execute generation of messages, including warnings and emergency alerts through the messaging system 145. These warnings and emergency alerts may be received by the driver, a surrounding vehicle or a centralized traffic management system. In some embodiments, the driver support actuation module 340 may determine a state of emergency when the driver state severity exceeds a predetermined level such that the driver is incapable of driving. In such an event, the driver support actuation module 340 may also activate an emergency response such as but not limited to, stopping the vehicle or transferring control of the vehicle from a driver mode to an autonomous mode.

In operation, the system 100 can be advantageously used to detect driver state and risk-level based on glucose levels and other physiological and environmental factors of the driver of the vehicle and then use the information to determine whether/when/how to intervene, including in some cases, an automatic transfer between autonomous vehicle control and driver control. The various components of the system 100 work together in ways described below to achieve such functionality.

The CGM device 120 worn by the driver measures the real-time glucose level of the driver and transmits the measurements to the receiver 142 in the driver monitoring system 140. Similarly, the one or more physiological sensors 130 worn by the driver measures the real-time physiological parameters of the driver and transmits the measurements to the receiver 142. The receiver 142 then feeds the measurements of the glucose levels and the physiological parameters of the driver to the insulin effect estimation module 304 in the machine-readable instruction set, which is stored in the non-transitory computer-readable memory 148 of the driver monitoring system 140. The measurements of glucose levels and physiological parameters of the driver are inputted to the driver responsiveness estimation module 310.

Additionally, the optional driver behavior detection module 302 may detect images of the driver's face, upper body, and feet using the image sensor 190. The driver behavior detection module 302 may then apply OpenPose, a computer vision tool to extract facial and whole-body features indicating the driver behavior and posture at any given time, which is then processed by a machine learning algorithm to estimate the driver behavior and posture. At the same time, the optional comorbid condition detection module 306 may receive weight measurements from a pressure sensor (not shown) embedded in the seat of the vehicle.

The driver responsiveness estimation module 310 may receive the estimated driver behavior and posture from the optional driver behavior detection module 302 and weight measurements of the driver from the comorbid condition detection module 306, in addition to the measurements of glucose levels and physiological parameters of the driver from the insulin effect estimation module 304. The driver responsiveness estimation module 310 classifies the information received from the inputs into different driver states based on the glucose levels of the driver, which maybe— severely hypoglycemic state, hypoglycemic state, euglycemic, hyperglycemic and severely hyperglycemic based on different ranges of glucose levels. The driver responsiveness estimation module 310 estimates the degree of responsiveness of the driver in real-time based on the inputs. The impairment level prediction module 320 then compares the estimated degree of responsiveness of the driver with a database of human responsiveness at various levels of glucose concentration in the blood to determine the degree of impairment of the driver in real-time based on whether the driver responsiveness meets or exceeds a predetermined threshold. For example, the impairment level prediction module 320 may determine that the driver is impaired if the driver responsiveness is less than 75% or mildly impaired if the driver responsiveness is greater than 75% but less than 95%.

The driver state severity prediction module 330 receives driver performance characteristics information from the driver performance characteristics module 332 and information on features of the driving environment from the driving environment characteristics module 334. As discussed above, the driver performance characteristics information includes data related to driver performance characteristics such as driver steering handling, braking and acceleration timing in different traffic conditions, while the features of the driving environment are determined from images of the surrounding driving environment such as but not limited to, surrounding cars, traffic signs and signals, lane markers and any road obstacles captured by the image sensor 190. The driver state severity prediction module 330 analyzes the degree of impairment of the driver in real-time with the driver performance characteristics information and the features of the driving environment to predict the severity of the driver state affecting driving performance and a real-time risk level associated with the driver state based on the severity of the driver state. The driver state severity prediction module 330 may utilize one or more machine learning and statistical techniques, described above, for this purpose.

Based on the determination of the severity of the driver state affecting driving performance and the associated risk-level, the driver support actuation module 340 determines an appropriate response, which may be a null response, stopping the vehicle or transferring control of the vehicle from a driver mode to an autonomous mode. The driver support actuation module 340 generates messages through the messaging system 145 such as, but not limited to, visual reading indicating the glucose level of the driver, warnings regarding severity of the driver state, future impairment episodes, and emergency alerts indicating that the driver state severity exceeds a predetermined level such that the driver is incapable of driving. These emergency alerts are received by the driver, a surrounding vehicle or a centralized traffic management system.

Figure 4:
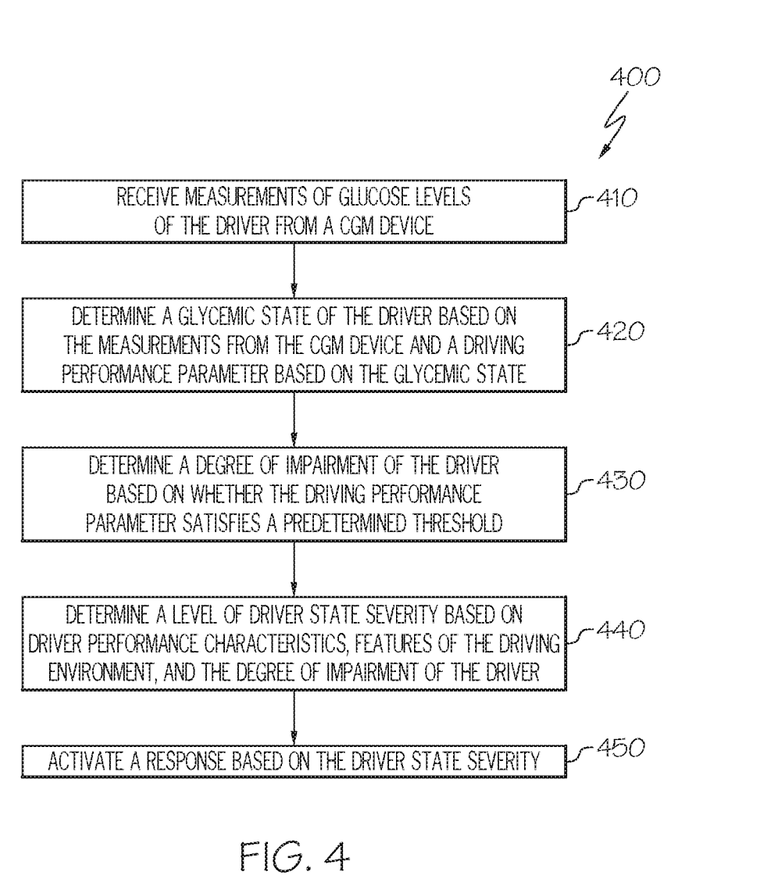
FIG. 4 depicts a block diagram for the method of controlling the vehicle based on glucose levels of a driver of the vehicle, according to one or more embodiments shown and described herein.

FIG. 4 depicts a block diagram for a method 400 of detecting driver state based on glucose levels of a driver of the vehicle. In block 410, the measurements of glucose levels of the driver of the vehicle are received by the driver monitoring system from the CGM device. The driver monitoring system thus may accumulate both current glucose levels as well as historical glucose levels of the driver over a period of time. In block 420, a glycemic state of the driver is determined by the driver monitoring system based on the measurements of the glucose levels. In some embodiments, the different glycemic states may be categorized as severely hypoglycemic (less than 56 mg/dL), hypoglycemic (56-70 mg/dL), euglycemic (71-179 mg/dL), hyperglycemic (180-300 mg/dL) and severely hyperglycemic (greater than 300 mg/dL). The driver monitoring system then determines a driving performance parameter based on the glycemic state. The driver monitoring system may incorporate information regarding other physiological parameters of the driver to determine the driving performance parameter. The other physiological parameters may be measured by a singular or a plurality of physiological sensors and include body temperature, drowsiness, blood pressure, heart rate, respiratory rate, blood oxygen level, electroencephalographic activity, electromyography activity, and gastric activity of the vehicle driver. The driving performance parameter is driver responsiveness related to vehicle acceleration variability, vehicle braking variability, and variability in detecting and negotiating road conditions.

In block 430, the driver monitoring system determines a degree of impairment of the driver based on whether the driving performance parameter satisfies a predetermined threshold. In some embodiments, the predetermined threshold relates to a range of driver responsiveness such that different levels of impairments are determined based on whether the driver responsiveness is above, within or below the range. For example, if the driver responsiveness is less than 75%, the driver may be deemed impaired to drive or if the driver responsiveness is greater than 75% but less than 95%, the driver may be deemed mildly impaired.

In block 440, the driver monitoring system determines a level of driver state severity based on driver performance characteristics, features of the driving environment, and the degree of impairment of the driver. In some embodiments, a risk-level associated with the driver state affecting driving performance may also be determined. In some embodiments, the driver performance characteristics are determined, using a machine-learning algorithm based on predictive patterns between driving performance of the driver and glucose levels and the other physiological parameters over time. The features of the driving environment are determined from images of the surrounding driving environment, such as but not limited to, surrounding cars, traffic signs and signals, lane markers and any road obstacles.

In block 450, the driver monitoring system activates a response based on the driver state severity. In some embodiments, the driver monitoring system may generate a message to alert a recipient if the driver state severity exceeds a predetermined level. In some embodiments, a state of emergency may be determined when the driver state severity exceeds a predetermined level. The driver monitoring system then activates an emergency response based on the state of emergency. In some embodiments, the emergency response may be stopping the vehicle or transferring control of the vehicle from a driver mode to an autonomous mode. In some embodiments, the emergency response may also be generating a warning or emergency alert to the driver, a surrounding vehicle or a centralized traffic management system.

The systems and methods described herein can be beneficially used towards improving driver behavior. At-risk driver behavior is successfully measured in individual drivers with wearable and in-vehicle sensor technology during continuous real-world driving. Appropriate intervention mechanisms are determined based on such measurements. The in-vehicle CGM devices and other physiological sensors can further help determine the level of control of glucose and other physiological parameters needed to produce meaningful improvement in driving performance. The continuous monitoring and detection of driver state techniques can be combined with machine learning methods to predict current and future impairment episodes. Ultimately, the system can develop a database of individual driver behavior and performance and health metrics, make momentary assessments during real-world driving and deliver meaningful feedback and advice to the driver.

It is noted that the terms "substantially" and "about" may be utilized herein to include the inherent degree of uncertainty that may be attributed to any quantitative comparison, value, measurement, or other representation. These terms are also utilized herein to represent the degree by which a quantitative representation may vary from a stated reference without resulting in a change in the basic function and intended scope of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method of detecting driver state based on glucose levels of a driver of the vehicle, the method comprising:
   receiving measurements of glucose levels of the driver from a continuous glucose monitoring (CGM) device;
   determining a glycemic state of the driver based on the measurements;
   determining a driving performance parameter based on the glycemic state;
   determining a degree of impairment of the driver based on whether the driving performance parameter satisfies a predetermined threshold by comparing with known values of the driving performance parameter at different glucose levels;
   determining a level of driver state severity based on driver performance characteristics, features of the driving environment, and the degree of impairment of the driver; and
   activating a response based on the driver state severity.

2. The method of claim 1, wherein the glycemic state of the driver relates to the following: severely hypoglycemic, hypoglycemic, euglycemic, hyperglycemic and severely hyperglycemic.

3. The method of claim 1, wherein the driving performance parameter is driver responsiveness related to at least one of the following: vehicle acceleration variability, vehicle braking variability, and variability in detecting and negotiating road conditions.

4. The method of claim 3, wherein the predetermined threshold relates to a range of driver responsiveness such that different levels of impairments are determined based on whether the driver responsiveness is above, within or below the range.

5. The method of claim 1, wherein the driver performance characteristics are determined, using a machine-learning algorithm based on predictive patterns between driving performance of the driver and glucose levels and other physiological parameters over time.

6. The method of claim 1 further comprising:
   determining a state of emergency when the driver state severity exceeds a predetermined level; and
   activating an emergency response based on the state of emergency.

7. The method of claim 6, wherein the emergency response further comprises at least one of the following:
   stopping the vehicle; and
   transferring control of the vehicle from a driver mode to an autonomous mode.

8. The method of claim 1 further comprising:
   generating a message to alert a recipient if the driver state severity exceeds a predetermined level.

9. A system of driver state detection based on glucose levels of a driver of the vehicle, the system comprising:
   a continuous glucose monitoring (CGM) device configured to sense and make measurements of glucose levels of the driver, the CGM device comprising:
      a transmitter configured to transmit the measurements of glucose levels of the driver; and
   a driver monitoring system communicatively coupled to the CGM device, the driver monitoring system comprising:
      one or more computing devices communicatively coupled to a receiver, each of the one or more computing devices comprising a processor and a non-transitory computer-readable memory storing a machine-readable instruction set that when executed by the processor causes the driver monitoring system to perform at least the following:
         receive measurements of glucose levels of the driver from the transmitter;
         determine a glycemic state of the driver based on the measurements;
         determine a driving performance parameter based on the glycemic state;

determine a degree of impairment of the driver based on whether the driving performance parameter satisfies a predetermined threshold by comparing with known values of the driving performance parameter at different glucose levels;

determine a level of driver state severity based on driver performance characteristics, features of the driving environment, and the degree of impairment of the driver; and activate a response based on the driver state severity.

10. The system of claim 9, wherein the glycemic state of the driver relates to the following: severely hypoglycemic, hypoglycemic, euglycemic, hyperglycemic and severely hyperglycemic.

11. The system of claim 9, wherein the driving performance parameter is driver responsiveness related to at least one of the following: vehicle acceleration variability, vehicle braking variability, and variability in detecting and negotiating road conditions.

12. The system of claim 11, wherein the predetermined threshold relates to a range of driver responsiveness such that different levels of impairments are determined based on whether the driver responsiveness is above, within or below the range.

13. The system of claim 9, wherein the driver performance characteristics are determined, using a machine-learning algorithm based on predictive patterns between driving performance of the driver and glucose levels and other physiological parameters over time.

14. The system of claim 9 further comprising:
a physiological sensor worn by the driver and communicatively coupled to the driver monitoring system, the physiological sensor configured to measure physiological parameters of the driver.

15. The system of claim 14, wherein the physiological sensor measures at least one of the following: body temperature, drowsiness, blood pressure, heart rate, respiratory rate, blood oxygen level, electroencephalographic activity, electromyography activity, and gastric activity.

16. The system of claim 9, wherein the driver monitoring system further comprises:
a messaging system configured to generate a message to alert a recipient if the driver state severity exceeds a predetermined level.

17. The system of claim 9, wherein the machine-readable instruction set when executed by the processor further causes the driver monitoring system to:
determine a state of emergency when the driver state severity exceeds a predetermined level; and
activate an emergency response based on the state of emergency, wherein the emergency response further comprises at least one of the following: stopping the vehicle; and transferring control of the vehicle from a driver mode to an autonomous mode.

18. A driver monitoring system comprising:
one or more computing devices communicatively coupled to a CGM device, each of the one or more computing devices comprising a processor and a non-transitory computer-readable memory storing a machine-readable instruction set that when executed by the processor causes the driver monitoring system to perform at least the following:
receive measurements of glucose levels of a driver from the CGM device;
determine a glycemic state of the driver based on the measurements;
determine a driving performance parameter based on the glycemic state;
determine a degree of impairment of the driver based on whether the driving performance parameter satisfies a predetermined threshold by comparing with known values of the driving performance parameter at different glucose levels;
determine a level of driver state severity based on driver performance characteristics, features of the driving environment, and the degree of impairment of the driver; and
activate a response based on the driver state severity; and
a messaging system configured to generate a message to alert a recipient if the driver state severity exceeds a predetermined level.

19. The driver monitoring system of claim 18, wherein:
the glycemic state of the driver relates to the following: severely hypoglycemic, hypoglycemic, euglycemic, hyperglycemic and severely hyperglycemic;
the driving performance parameter is driver responsiveness related to at least one of the following: vehicle acceleration variability, vehicle braking variability, and variability in detecting and negotiating road conditions;
the predetermined threshold relates to a range of driver responsiveness such that different levels of impairments are determined based on whether the driver responsiveness is above, within or below the range; and
the driver performance characteristics are determined, using a machine-learning algorithm based on predictive patterns between driving performance of the driver and glucose levels and other physiological parameters over time.

20. The driver monitoring system of claim 19, wherein the machine-readable instruction set when executed by the processor further causes the driver monitoring system to:
determine a state of emergency when the driver state severity exceeds a predetermined level; and
activate an emergency response based on the state of emergency, wherein the emergency response further comprises at least one of the following: stopping the vehicle; and transferring control of the vehicle from a driver mode to an autonomous mode.

* * * * *

UNITED STATES PATENT AND TRADEMARK OFFICE
CERTIFICATE OF CORRECTION

| | | |
|---|---|---|
| PATENT NO. | : 10,583,842 B1 | Page 1 of 1 |
| APPLICATION NO. | : 16/150506 | |
| DATED | : March 10, 2020 | |
| INVENTOR(S) | : Pujitha Gunaratne | |

It is certified that error appears in the above-identified patent and that said Letters Patent is hereby corrected as shown below:

In the Specification

In Column 7, Line(s) 28 & 29, delete "310" and insert --310.--, therefor.

Signed and Sealed this
Twenty-third Day of June, 2020

Andrei Iancu
*Director of the United States Patent and Trademark Office*